United States Patent [19]

Hattori

[11] 4,402,311
[45] Sep. 6, 1983

[54] ENDOSCOPE FOR MEDICAL TREATMENT

[75] Inventor: Shinichiro Hattori, Tokyo, Japan

[73] Assignee: Olympus Optical Co., Ltd., Tokyo, Japan

[21] Appl. No.: 131,626

[22] Filed: Mar. 19, 1980

[30] Foreign Application Priority Data

Mar. 30, 1979 [JP] Japan .................... 54-38181

[51] Int. Cl.$^3$ .................................... A61B 1/00
[52] U.S. Cl. .................................... 128/4; 128/736
[58] Field of Search .................... 128/4–8, 128/207.21, 207.22, 303.1, 401, 399, 395, 398, 804, 736

[56] References Cited

U.S. PATENT DOCUMENTS

| 3,785,383 | 1/1974 | Dotto | 128/395 |
|---|---|---|---|
| 3,948,269 | 4/1976 | Zimmer | 128/303.1 |
| 4,016,886 | 4/1977 | Doss et al. | 128/399 |
| 4,138,998 | 2/1979 | Nowogrodzki | 128/303.17 |
| 4,154,246 | 5/1979 | LeVeen | 128/804 |
| 4,159,411 | 6/1979 | Ellersick | 128/395 |
| 4,160,455 | 7/1979 | Law | 128/401 |
| 4,170,997 | 10/1979 | Pinnow et al. | 128/395 |
| 4,182,313 | 1/1980 | Aslan | 128/736 |
| 4,196,734 | 4/1980 | Harris | 128/303.17 |

FOREIGN PATENT DOCUMENTS

| P32763D | 9/1951 | Fed. Rep. of Germany | 128/303.1 |
|---|---|---|---|
| 2815156 | 10/1978 | Fed. Rep. of Germany | 128/401 |
| 2731659 | 1/1979 | Fed. Rep. of Germany | 128/303.1 |
| 52-25572 | 7/1977 | Japan | 128/401 |

OTHER PUBLICATIONS

Meyer R. A., A Laser Stimulator for the Study of Cutaneous Thermal & Pain Sensation, IEEE Trans on Biomed. Engr., vol. BME-23, No. 1, pp. 54–60, 1/76.

Primary Examiner—William E. Kamm
Assistant Examiner—Max F. Hindenburg
Attorney, Agent, or Firm—Frishauf, Holtz, Goodman & Woodward

[57] ABSTRACT

An endoscope for medical treatment which comprises a specific distal end portion which includes a thermal energy generating means for providing thermal energy to the outside from the distal end portion; a temperature detecting means mounted on the distal end portion which detects the temperature of a body part to be heated by the thermal energy and provides a detected signal corresponding to the temperature of the heated body part; and a control means for feedback controlling the thermal energy generating means in response to the detected signal so as to maintain the temperature of the heated body part at a predetermined level.

13 Claims, 11 Drawing Figures

ENDOSCOPE FOR MEDICAL TREATMENT

BACKGROUND OF THE INVENTION

The present invention relates to an endoscope which is capable of medically treating an affected body part by partial heating of a body cavity.

It has been recently discovered that malignant tumors, such as cancer, lose the ability to multiply at temperatures over 40° C. Thus, it is possible to treat cancer by heating the affected part. Such a treatment method was reported at the thirty-first convention of the Japanese Society of Cellular Biology held at Osaka University on Nov. 14, 1978 initiated by the research group of the Japan National Institute of Health. Based on this finding, an endoscope has been conventionally proposed having an air supply inlet and a suction outlet at the distal end portion of an endoscope wherein warmed air or water is blown from the air supply inlet to a part of the body cavity, and the warmed air or water is exhausted from the suction outlet, thereby heating a part of the body cavity, that is, the affected part. However, such a conventional endoscope does not have a control means for controlling the temperature of the warmed air or water blown from the air supply inlet. Thus, it has been impossible to heat the part of the body cavity at a constant temperature. There has also been proposed a radiant heating device for heating the affected part utilizing heat rays through glass fiber. Such a device is, for example, disclosed in Japanese Patent Publication No. 25572/77 wherein heat rays from a halogen lamp are converged by a predetermined method, and the affected part is heated through glass fiber. This reference, however, discloses no means for maintaining the affected part at a constant temperature.

Accordingly, it has been impossible, with a conventional device, to develop a practical treating method for destroying cancer cells alone by maintaining the part of the body cavity at a specific temperature at which normal cells of a human body thrive but at which cancer cells will be destroyed.

It is also a general practice to surgically remove the affected part by inserting an electric scalpel through the channel of an endoscope. The purpose of this is to remove the affected part by surgery. Therefore, the temperature of the body part touched by the electric scalpel will be raised to several hundred degrees. Thus, it is dangerous in that normal cells which contact the electric scalpel will be destroyed. Further, since the electric scalpel is inserted through the channel of an endoscope, the shape of the electric scalpel is limited to a certain range. Accordingly, the removal of the affected part is impossible if the shape of the malignant growth is, for example, flat. It is sometimes impossible to remove the part for preventing hazards such as excessive bleeding depending on the location of the tumor.

SUMMARY OF THE INVENTION

The present invention has been made to overcome these problems and has for its object to provide an endoscope which is capable of heating a part of a body cavity to any predetermined temperature and which can control the temperature with ease.

For achieving the above-mentioned object, an endoscope for medical treatment comprises an endoscope with a distal end portion; a thermal energy generating means for providing thermal energy to the outside from the distal end portion; a temperature detecting means mounted on the distal end portion which detects the temperature of the part to be heated by the thermal energy and provides a detection signal corresponding to the temperature of the heated part; and a control means for feedback controlling the thermal energy generating means in response to the detection signal and for maintaining the heated part at a predetermined temperature.

In accordance with an endoscope of such construction, it is possible to automatically maintain the part to be heated at a predetermined temperature, such as between 40° C. and 43° C. Thus, it is possible to effectively destroy a malignant tumor without damaging normal cells.

The reference data for determining the value of the predetermined temperature can be arbitrarily selected. Accordingly, it is possible to automatically control, freely and correctly, the temperature of the part to be heated at a desired value within the range of energy obtainable with a provided heating means.

DETAILED DESCRIPTION OF THE PREFERRED EMBODIMENTS

Preferred embodiments of the present invention will now be described referring to the accompanying drawings. For the purpose of brevity, similar numerals designate similar parts in the various drawings. That is, parts designated by the same numeral are interchangeable in all of the figures.

Figure 1:
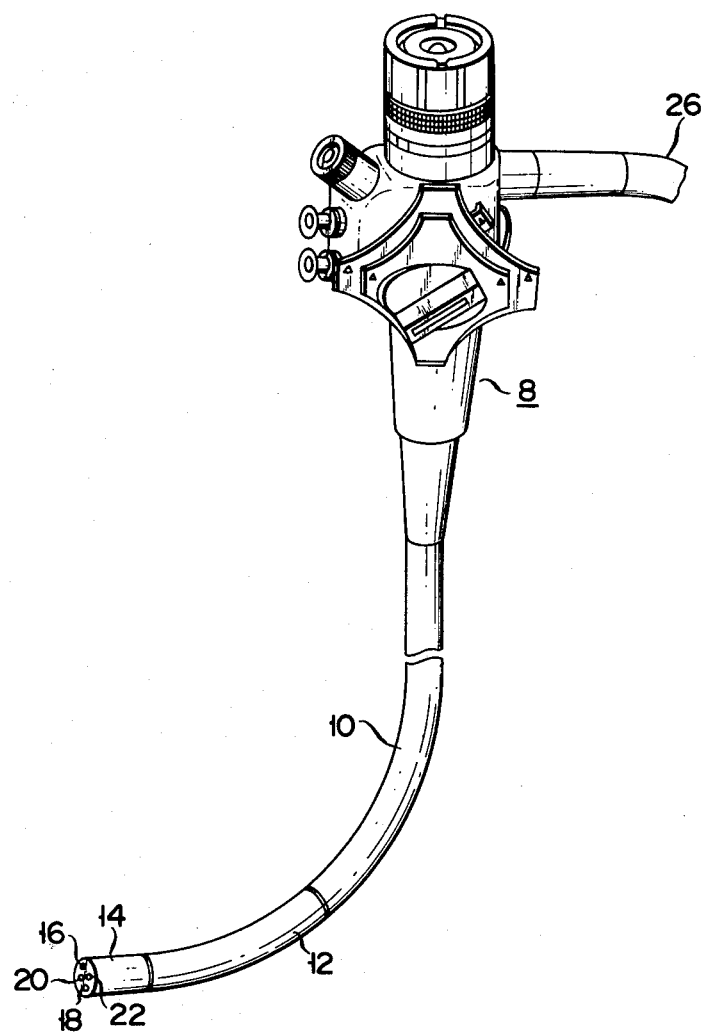
FIG. 1 shows the outer appearance of an endoscope to which the present invention can be applied.

FIG. 1 shows the outer appearance of an endoscope to which the present invention can be applied. The distal end portion 14 is coupled to a flexible tube 10 communicating with a manipulating part 8 through a bendable section or an insertion section 12. The light window of a light guide 16 and the observation window of an observation optical system 18 are disposed at the distal end portion 14. These components 8 to 18 are of conventional construction. The portion 14 also includes an infrared ray irradiator 20 and a temperature sensor 22. The portion 14 of such a configuration may be inserted into parts such as a uterus with cancer cells.

Figure 2:
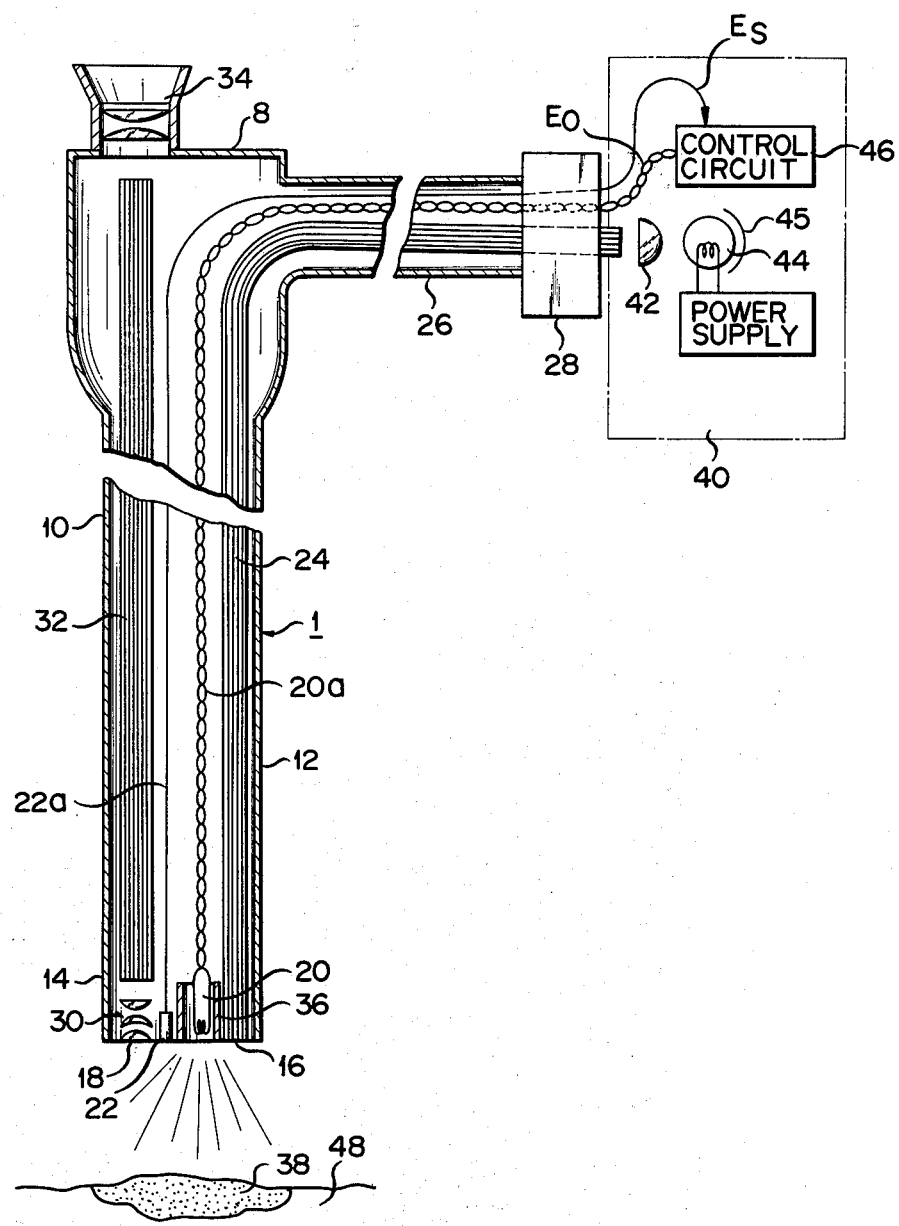
FIG. 2 is a partial sectional view of the endoscope shown in FIG. 1.
Figure 3:
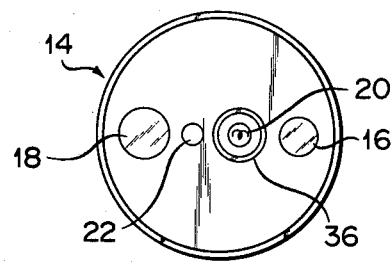
FIG. 3 shows the end face of the distal end portion of the endoscope shown in FIG. 1.
Figure 5:
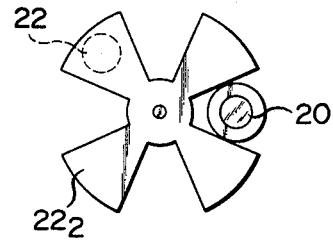
FIGS. 4 and 5 show the construction for mechanically chopping infrared rays at the distal end portion.
Figure 4:
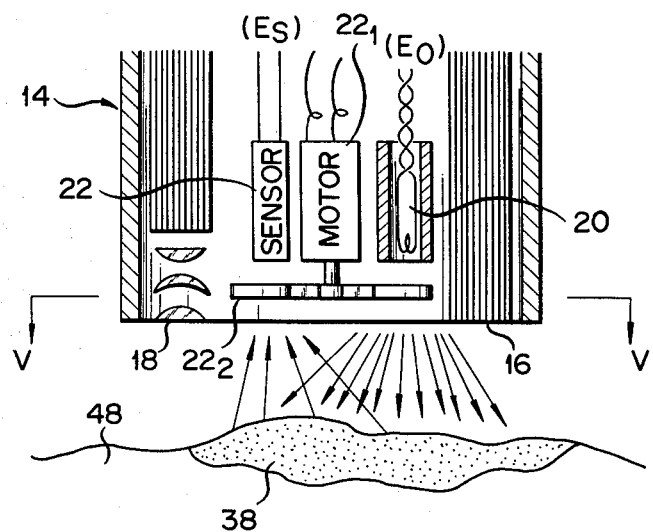

FIG. 2 is a partial sectional view of the endoscope shown in FIG. 1, and FIG. 3 shows the end face of the distal end portion 14 shown in FIG. 1. As seen from FIG. 3, the light window 16 and the observing window 18 are disposed at the distal end portion 14. As shown in FIG. 2, the light window 16 communicates with a connector 28 through an optical fiber 24 disposed inside the insertion section 12 and a universal cord 26. The observing window 18 communicates with an eyepiece 34 of the manipulating part 8 through an objective lens 30 and an optical fiber 32 disposed inside the insertion section 12. The infrared ray irradiator 20 surrounded by an adiabatic or thermal insulating cylinder 36 constitutes a means for supplying heat and is mounted to the distal end portion 14 of the endoscope body 1 of this construction. The temperature sensor 22 is disposed adjacent to the adiabatic cylinder 36 as a means for providing a signal corresponding to the temperature of an affected part 38 to be heated by the infrared ray irradiator 20 by detecting the temperature of the part 38 at the inner wall of the body cavity. The irradiator 20 and the sensor 22 are connected to the connector 28 by lead wires 20a and 22a disposed inside the insertion section 12 and the universal cord 26. An adiabatic wire, such as a twisted pair wire coated with Teflon, is used for the lead wire 20a. The connector 28 is detachably coupled to a power source device 40. A light source 44 is disposed in the power source device 40 which faces the optical fiber 24 through a converging lens 42. The light source 44 is not limited to the above construction, but a lamp of a tungsten/nichrome double filament type with a reflection mirror 45 set at its back can be used. A non-contact temperature sensor, such as a pyroelectric type infrared ray sensor, can be used as the non-contact temperature sensor 22. One example of such a sensor is Pyroelectric Metal on Electric Conductor (PEC) construction type available from SANYO ELECTRIC CO., Japan. If a pyroelectric type infrared ray sensor is used as the sensor 22 for detecting the infrared rays from the body whose temperature is to be measured, it is necessary to chop the infrared rays incident on the sensor. A chopper for this purpose can be constructed electrically, but it can also be conveniently constructed mechanically. FIGS. 4 and 5 show a case where the chopping is performed mechanically. That is, a screening fin $22_2$ rotated by a motor $22_1$ is disposed at a fixed position between the irradiator 20 and the sensor 22. The infrared rays or thermal irradiation incident on the sensor from the affected part 38 are chopped by the rotation of the fin $22_2$.

When the infrared rays from the irradiator 20 are reflected by the affected part 38 and the surrounding cells 48 and are incident on the sensor 22, it becomes impossible to correctly detect the temperature of the affected part 38. Thus, it becomes impossible to maintain the affected part 38 at a predetermined temperature. In order to prevent this, the thermal energy supplied from the irradiator 20 to the affected part 38 is interrupted at intervals at which temperature control is not inconvenient, the temperature of the affected part 38 is detected when the irradiator 20 is not emitting thermal energy, and temperature control is effected on the basis of the result. For effecting this electrically, for example, the sensor 22 is rendered inactive by means such as an analog switch circuit while the irradiator 20 is energized. The temperature control can be performed in response to the signal output ($E_s$) from the sensor 22 while the irradiator 20 is rendered inactive. This may alternatively be performed mechanically. As seen from FIG. 5, the sensor 22 is screened off whenever the fin $22_2$ is not screening off the irradiator 20. When the fin $22_2$ is rotated through 45°, the irradiator 20 is screened off and the screen is removed from in front of the sensor 22. Thus, the sensor 22 is able to detect the temperature of the affected part 38 only while the infrared rays from the irradiator 20 do not irradiate the affected part 38, thereby facilitating precise temperature control.

For the sensor 22 to detect the infrared rays from the irradiator 20, the light source 44 preferably does not emit infrared rays, because a desired temperature control cannot be obtained if the infrared energy detected by the sensor 22 is not the energy from the irradiator 20 only. If necessary, a filter (not shown) for absorbing electromagnetic waves of lower frequency range of the infrared rays may be interposed between the light source 44 and the light window 16. Alternatively, the optical fiber 24 may comprise one which blocks infrared rays. The light emitted from the light window 16 may be electromagnetic waves of any frequency as long as it is within the visible range, so that the normal cells 48 can be distinguished from the affected part 38 by observation. It is apparent that a temperature sensitive device of any other type may be used for the sensor 22.

The power source device 40 is coupled with the lead wires 20a and 22a, and includes a control circuit 46 or a control means for adjusting thermal energy, or controlling the output of the irradiator 20, in accordance with a detected signal $E_s$ derived from the sensor 22. The particular construction of the control circuit 46 will be described later, and the operation of the endoscope shown in FIG. 2 will now be described.

For heating the affected part 38, such as cancer cells in the inner wall of a body cavity, the insertion section 12 of the endoscope body 1 is inserted within the body cavity and the distal end portion 14 is opposed to the affected part 38. Under these conditions, the infrared rays are emitted from the infrared ray irradiator 20 in response to an output signal $E_o$ from the control circuit 46. The temperature of the affected part 38 is thus raised. The non-contact temperature sensor 22 detects the temperature of the affected part 38. The detected signal $E_s$ is fed back to the control circuit 46 for controlling the output of the irradiator 20. Thus, the temperature of the affected part 38 can be held constant, such as around 40° C., by the automatic control operation of this feedback mechanism. Accordingly, it is possible to destroy the abnormal cells of the affected part 38 without adversely affecting the normal cells 48 surrounding the affected part 38.

Figure 6:
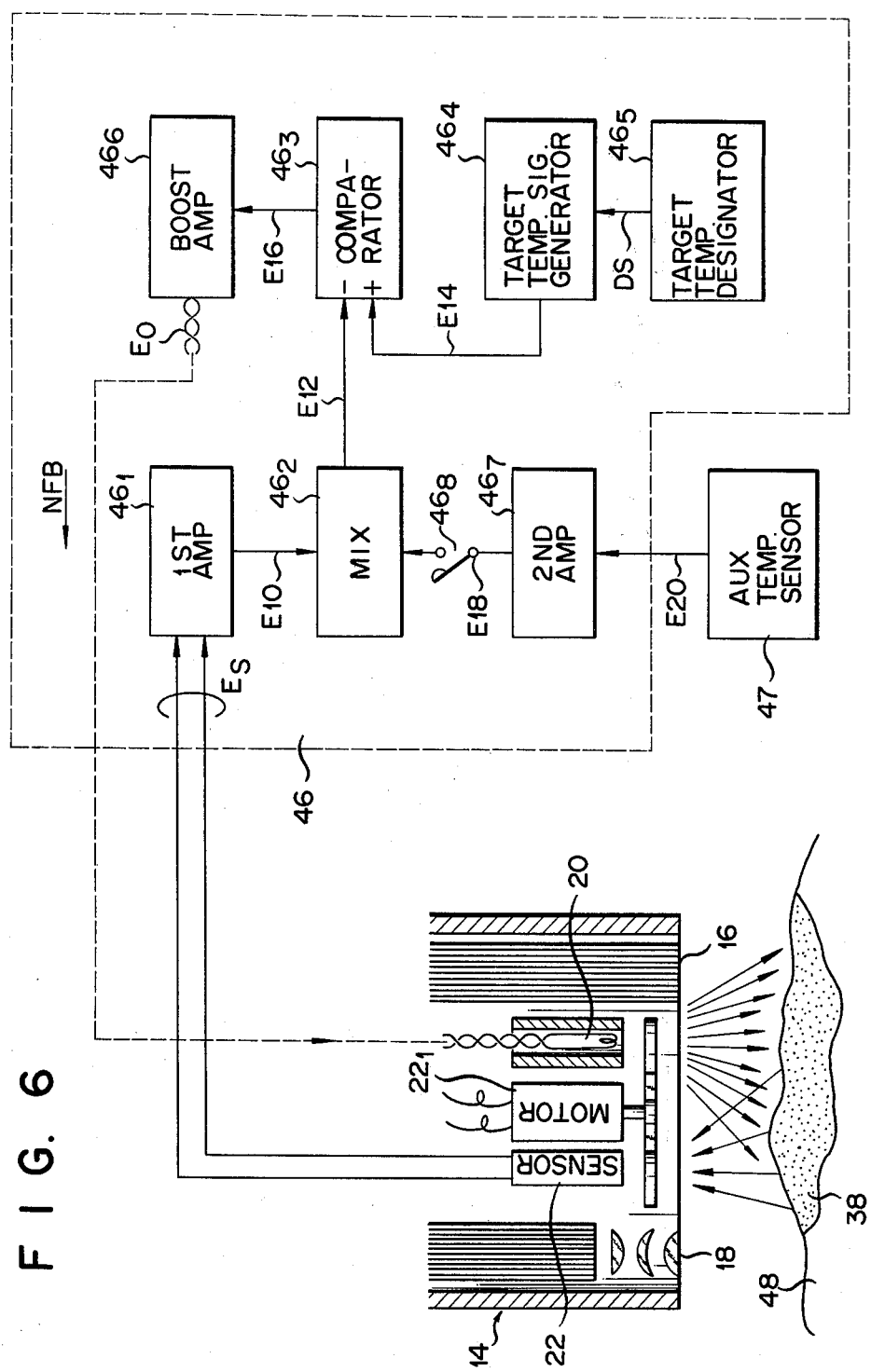
FIG. 6 is a block diagram illustrating a concrete construction of the control circuit shown in FIG. 2.

FIG. 6 shows an example of the construction of the control circuit 46 shown in FIG. 2. The detected signal $E_s$ is applied to a first amplifier $46_1$. The amplifier $46_1$ amplifies the signal $E_s$ and outputs a corresponding first signal E10, which is applied to a mixer $46_2$. The mixer $46_2$ mixes the signal at need and outputs a second signal E12. The signal E12 is applied to the inverted input or the comparison input of a comparator $46_3$. A third signal E14 from a target temperature signal generator $46_4$ is applied to the non-inverted or reference input of the comparator $46_3$. The level of the signal E14 is determined by a designation signal DS output from a target temperature designator $46_5$. The generator $46_4$ and the designator $46_5$ may comprise a suitable DC power source and a divider or variable resistor for voltage dividing the source potential.

The comparator $46_3$ compares the signals E12 and E14 and outputs a comparison output signal E16 corresponding to the difference E14−E12. The signal E16 is applied to a boost amplifier $46_6$. The amplifier $46_6$ boosts the signal E16 and provides the output signal $E_o$ to the irradiator 20. A fourth signal E18 is applied from a second amplifier 46₇ to the mixer 46₂ through a switch 46₈. The signal E18 corresponds to a fifth signal E20 provided by an auxiliary temperature sensor 47. When the switch 46₈ is turned off, E10=E12, and the temperature control of the affected part 38 is effected by the feedback loop of 22→46₁→46₂→46₃→46₆→20→38→22. The control target temperature in this case is determined by the designator 46₅.

Since the distance between the portion 14 and the affected part 38 is not constant, the temperature of the affected part 38 may not always correspond to the specific temperature designated by the designator 46₅. In such a case, the switch 46₈ is turned on, the temperature of the affected part 38 and its vicinity is detected by the sensor 47 (e.g., a thermistor thermometer), and the signal output from the sensor 47 corresponding to the detected temperature is provided to the feedback loop so that control errors due to variations of the distance between the portion 14 and the affected part 38 are compensated.

Although the above description has been made with reference to an analog servomechanism, a digital servomechanism may be utilized. In this case, an analog-to-digital converter is interposed between the mixer 46₂ and the comparator 46₃, and a digital-to-analog converter is interposed between the comparator 46₃ and the amplifier 46₆. In this case, a keyboard may be used as the designator 46₅ and an ROM code convertor may be used for the generator 46₄.

Figure 7:
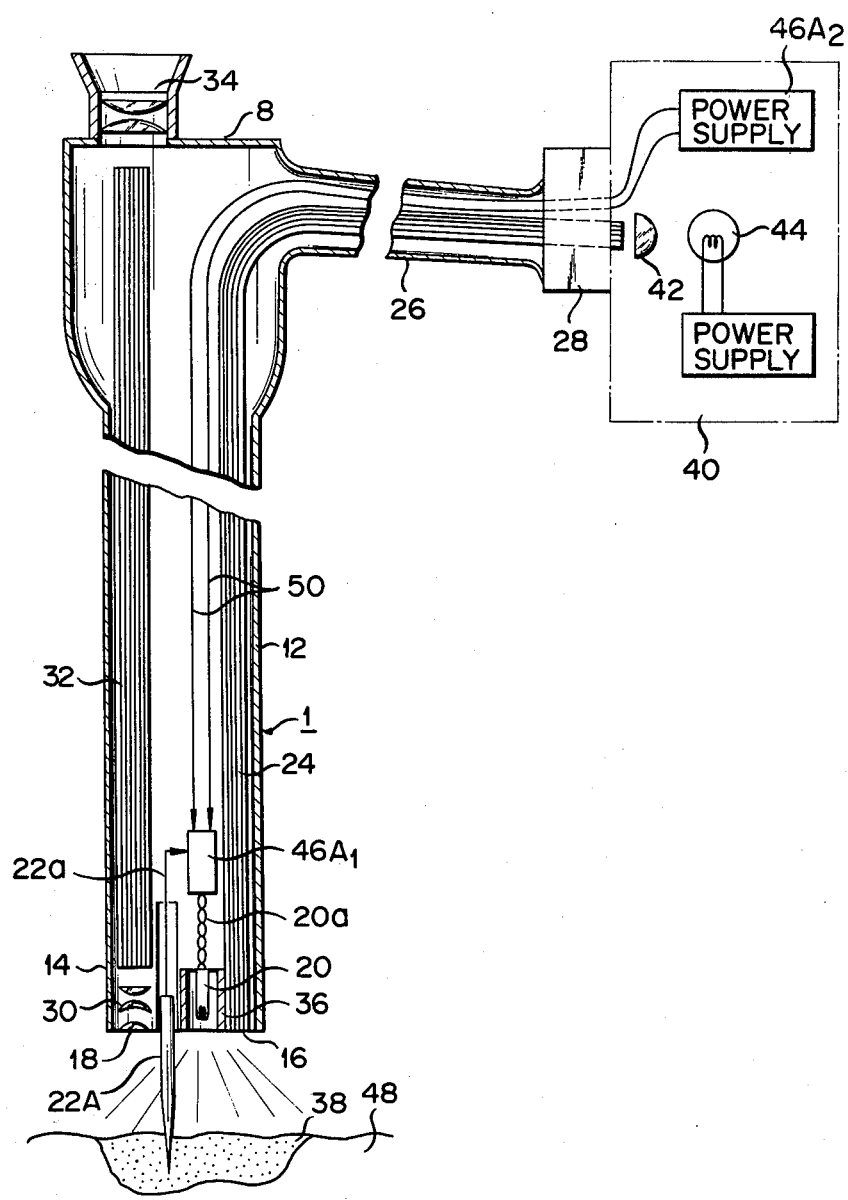
FIG. 7 shows a modification of the endoscope of FIG. 2.

FIG. 7 shows a modification of FIG. 2. Instead of the non-contact temperature sensor 22, a protruding needle-type temperature sensor 22A with a temperature responsive semiconductor element such as a thermistor is mounted on the portion 14. The needle-type temperature sensor 22A and the infrared ray irradiator 20 are electrically connected to a control circuit 46A₁ built into the insertion section 12 of the endoscope body 1. The control circuit 46A₁ is further connected to a power supply 46A₂ within the power source device 40 through a power feeder 50. With such a construction, it is possible to insert the needle type temperature sensor 22A into the affected part 38 by external manipulation using means such as a plunger after inserting the insertion section 12 into the body cavity, since the needle type temperature sensor 22A is accommodated in the portion 14. Thus, the temperature at the surface as well as inside the affected part 38 can be correctly detected so that the malignant cells can be destroyed deep within the affected part 38.

The needle-type temperature sensor 22A functions to secure the endoscope in a fixed position, as well as to detect the temperature. Thus, it is possible to emit the infrared rays from a constant distance from the affected part 38 for a prolonged time, so that the stability of the temperature control is improved. Instead of disposing the control circuit 46A₁ within the insertion section 12, the circuit 46A₁ can be disposed within the power source device 40 as seen in FIG. 2.

Figure 8:
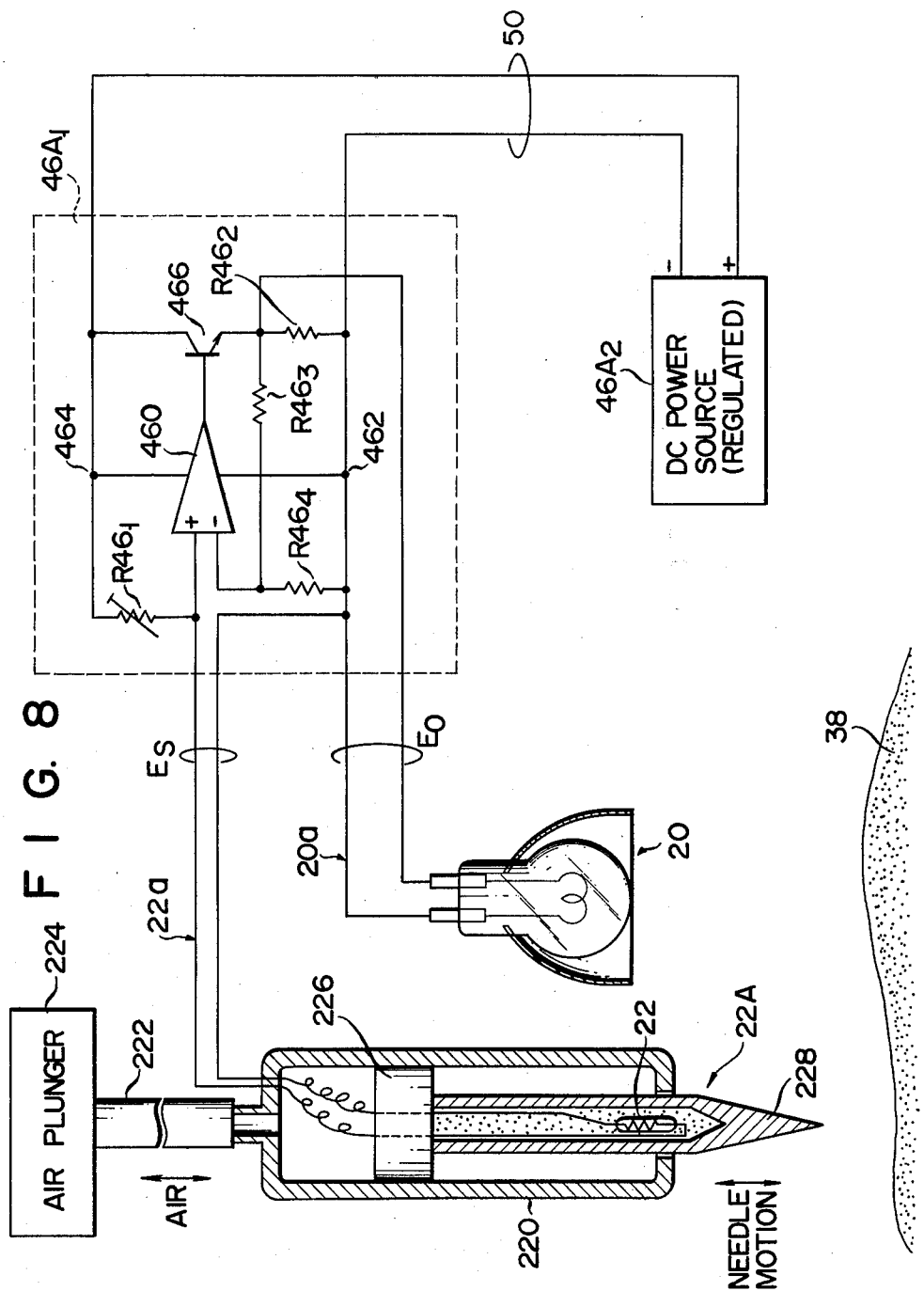
FIG. 8 shows the construction of the control circuit and the needle type temperature sensor shown in FIG. 7.

FIG. 8 shows the particular construction of the control circuit (control unit) 46A₁ and the needle-type temperature sensor 22A shown in FIG. 7. The sensor 22A has a cylinder 220 coupled through an air pump 222 to an air plunger 224, a piston 226 slidable within the cylinder 220 by air pressure from the plunger 244, a hollow metal needle 228 mounted on the piston 226, and a thermistor 22. As seen from FIG. 7, when the needle 228 is inserted into the affected part 38, by the air pressure from the plunger 224, the temperature inside the affected part 38 is transmitted to the thermistor 22 through the needle 228. The thermistor 22 shows a resistance value corresponding to this temperature. The terminal ends of the thermistor 22 are connected through the lead wire 22a to the non-inverted input of an OP amplifier 460 and a grounded circuit 462.

The non-inverted input of the OP amplifier 460 is connected to a positive power source circuit 464 through a resistor R46₁. The output of the amplifier 460 is connected to the base of an npn transistor 466. The collector of the transistor 466 is connected to the circuit 464 and the emitter is connected to the circuit 462 through a resistor R46₂. The emitter of the transistor 466 is connected through a resistor R46₃ to the inverted input of the amplifier 460. The inverted input is connected to the circuit 462 through a resistor R46₄. The circuits 462 and 464 are connected through the feeder 50 to the negative and positive electrodes of a voltage-stabilized DC power source 46A₂. The circuit 462 and the emitter of the transistor 466 are connected to the infrared ray irradiator 20 through the lead wire 20a.

The control circuit 46A₁ shown in FIG. 8 operates in the manner described below. Assume the needle 228 is inserted into the affected part 38 and the temperature of the affected part 38 is lower than the predetermined temperature such as 40° C. In this case, the resistance of the thermistor 22 is relatively high (as compared to the case wherein the temperature is high). Hence, the detected signal $E_s$ is great, as is the voltage potential at the non-inverted input of the amplifier 460 with reference to the circuit 462. The emitter potential of the transistor 466 also becomes higher, and the output signal $E_o$ becomes greater. Thus, the voltage supplied to the irradiator 20 is raised and the thermal energy provided to the affected part 38 from the irradiator 20 becomes greater. The temperature of the affected part 38 is raised. The temperature increase of the affected part 38 produces a resistance drop in the thermistor. From this the signal $E_s$ becomes smaller and then the signal $E_o$ also becomes smaller. The temperature increase of the affected part 38 is interrupted by a decrease in the signal $E_o$. The circuit 46A₁ ultimately stabilizes when the potentials of both inputs of the amplifier 460 are substantially the same. The potential of the non-inverted input of the amplifier 460 can be changed by the resistor R46₁. Therefore, by adjusting the resistance of R46₁, automatic control of the thermal energy supplied from the irradiator 20, or automatic temperature control of the affected part 38, can be effected.

The control circuit 46A₁ may be replaced with the control circuit 46 shown in FIG. 6. Since the circuit 46A₁ is simple in construction and has a small number of parts, it may be made compact in size and may be easily assembled within the insertion section 12 as shown in FIG. 7.

Figure 9:
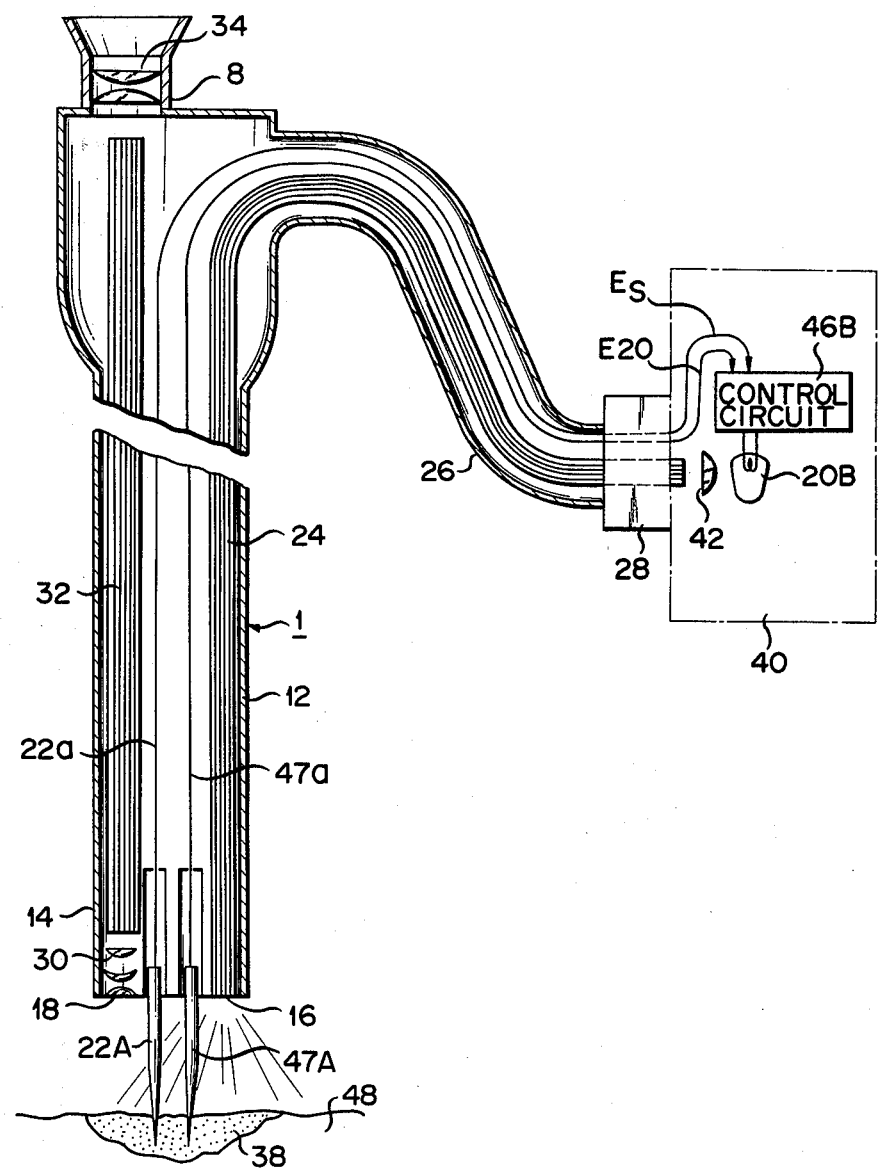
FIG. 9 shows a modification of the endoscope shown in FIG. 2 or 7.

FIG. 9 shows a modification of the construction shown in FIG. 2 or FIG. 7. A plurality of needle-type sensors 22A and 47A are mounted on the distal end portion 14, so as to retract or extend from it. They are connected through the lead wires 22a and 47a to the control circuit 46B of the power source device 40. A lamp 20B for emitting both infrared rays and visible light is connected to the control circuit 46B. This lamp opposes the end face of the optical fiber 24 through the converging lens 42.

With this construction, it is possible to insert a plurality of needle-type temperature sensors 22A and 47A into the affected part 38. Thus, the output signals corresponding to the temperature of a large area of the affected part 38 are applied to the control circuit 46B. The temperature of the affected part 38 is measured in the vicinity of the line connecting the sensor 22A with the sensor 47A. Temperature control is performed in response to the detected result. More particularly, the output energy of the lamp 20B is adjusted in response to the input signals $E_s$ and $E_{20}$ so that the affected part 38 is irradiated from the light window 16 through the optical fiber 24, thereby maintaining the affected part 38 at a predetermined temperature. When a light path switching means is disposed in the light window 16 for changing the direction of irradiation according to the signals $E_s$ and $E_{20}$ from the needle-type temperature sensors 22A and 47A, the temperature of the large area of the affected part 38 can be maintained at a constant level. Further, since the needle-type temperature sensors are plural in number, the position of the portion 14 can be more securely fixed relative to the affected part 38. Instead of a lamp for emitting both infrared rays and visible rays, it is also possible to dispose both an infrared ray lamp and a visible ray lamp. In this case, a half mirror is used for synthesizing the light, or the infrared rays and the visible rays may be switched by rotating a mirror through a predetermined angle.

For the light path switching means, a device disclosed in Japanese Utility Model publication No. 7829/73, title of which is "BENDABLE TUBE OF AN ENDOSCOPE" can be used. The assignee of this publication is the same as that of the present application.

Figure 10:
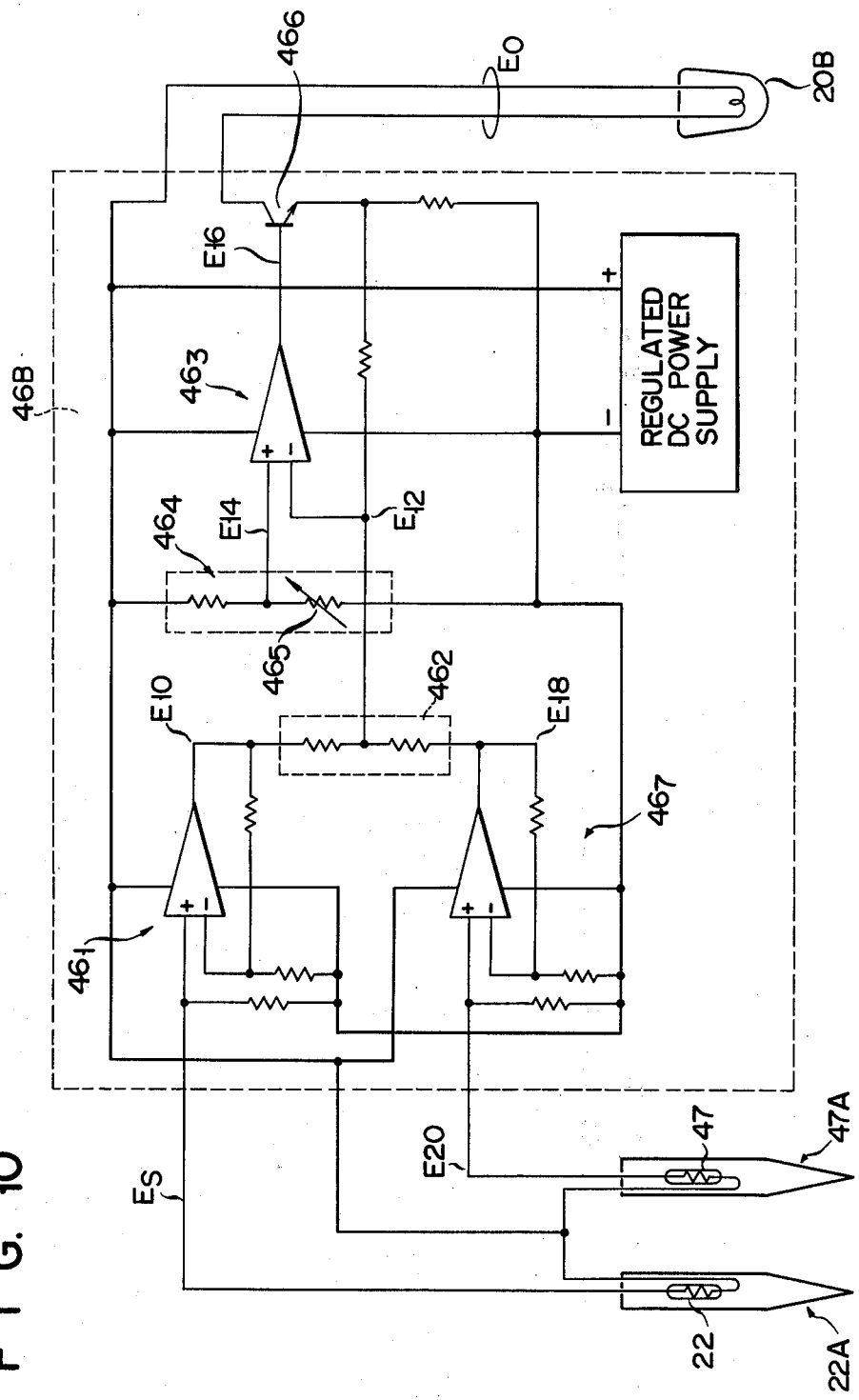
FIG. 10 shows the construction of the control circuit shown in FIG. 9.

FIG. 10 shows a particular construction of the control circuit 46B shown in FIG. 9. Since the construction almost corresponds to that described with reference to the control circuit 46 shown in FIG. 6, unnecessary further explanation will be avoided.

A signal $E_s$ derived from the thermistor 22 of the sensor 22A is amplified to a signal $E_{10}$ by the first amplifier $46_1$. Similarly, a signal $E_{20}$ derived from the thermistor 47 of the sensor 47A is amplified to a signal $E_{18}$ by the second amplifier $46_7$. The sensor 47A or the thermistor 47 correspond to the auxiliary temperature sensor 47 shown in FIG. 6. The signals $E_{10}$ and $E_{18}$ are converted to a signal $E_{12}$ through the mixer $46_2$. The signal $E_{12}$ is applied to the inverted input of the comparator $46_3$. A signal $E_{14}$ is applied from the target temperature signal generator $46_4$ to the non-inverted input of the comparator $46_3$.

The level of the signal $E_{14}$ can be changed by the variable resistor $46_5$. A signal $E_{16}$ is obtained as a result of a comparison by the comparator $46_3$. The signal $E_{16}$ is current boosted by an npn transistor $46_6$ and converted to the signal $E_o$ which is applied to the lamp 20B.

Although, by using an inverted amplifier for either of the amplifiers $46_1$ or $46_7$, temperature control is possible such that the temperature difference between the vicinity of the sensor 22A and that of the sensor 47A is constant.

Figure 11:
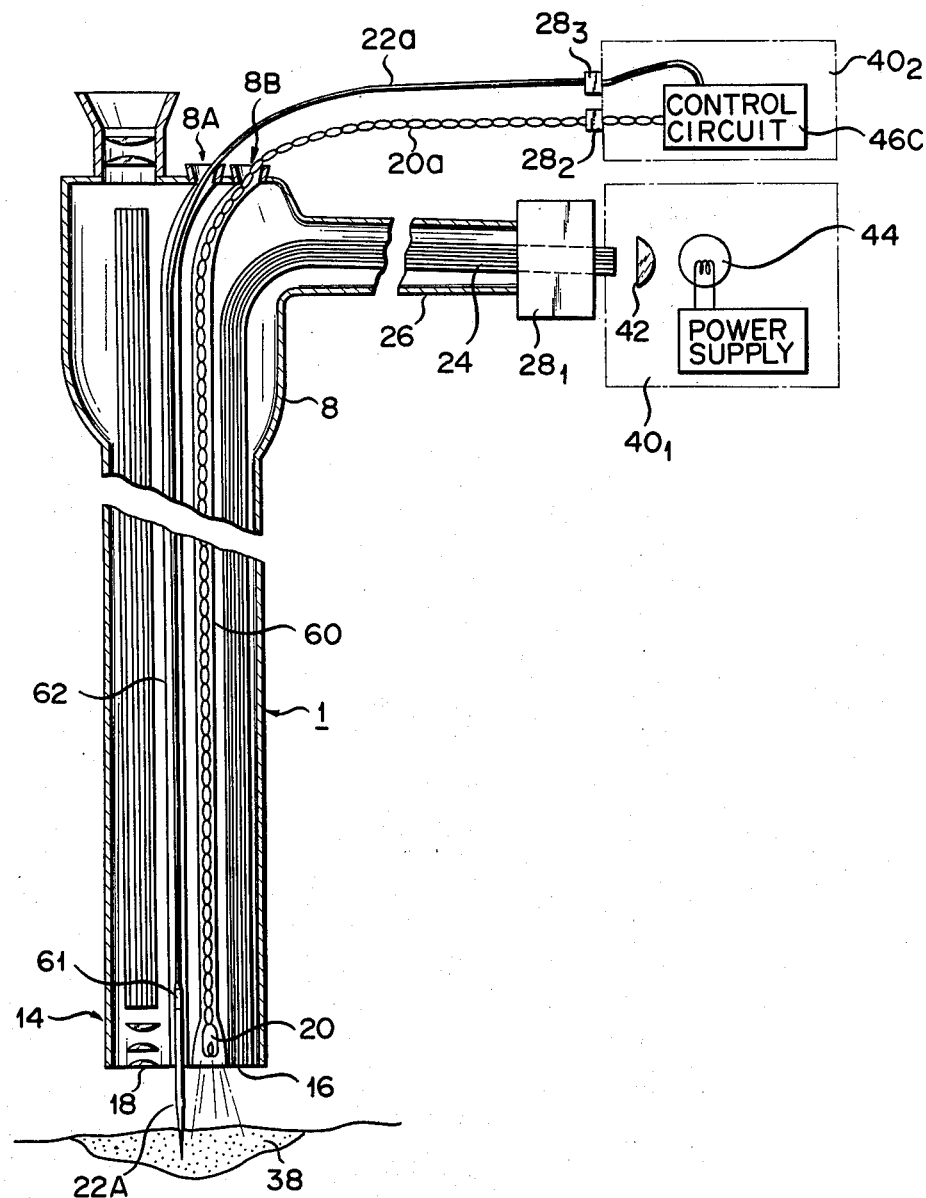
FIG. 11 shows a modification of the device of FIG. 7.

FIG. 11 shows a modification of FIG. 7. The endoscope includes lead tubes 60 and 62 from the manipulating part 8 to the portion 14. In the tube 60 is inserted a flexible lead wire 20a with the irradiator 20 mounted on one of its ends. Such a wire 20a may be obtained by twisting a teflon coated signal wire of 0.5 to 1.0 mm in diameter. In the tube 62 is inserted a lead wire 22a with the needle-type temperature sensor 22A secured by a jig 61 to one of its ends. In order to resist the reaction when the sensor 22A is inserted into the affected part 38, the lead wire 22a is preferably flexible but is rigid to a certain extent.

The lead wires 20a and 22a are connected through connectors $28_2$ and $28_3$ to an unit $40_2$ which includes a control circuit 46C. For removing the irradiator 20 and the sensor 22A from the endoscope 1, the lead wires 20a and 22a are pulled out of the tubes 60 and 62. For mounting, these are inserted into inserting inlets 8A and 8B.

The unit $40_2$ may be formed integrally with the power source device $40_1$ for supplying light to the optical fiber 24. In this case, the components $40_1$ and $40_2$ correspond to the power source device 40 of FIG. 7. The circuit 46C corresponds to the components $46A_1$ and $46A_2$ shown in FIG. 7.

As has been described, in accordance with the present invention, a part of the body cavity can be heated to a desired temperature since a thermal energy generating means and a temperature detecting means for detecting the temperature at the heated part are disposed at the distal end portion of the endoscope body. The thermal energy irradiating output is adjusted in response to a signal provided by the temperature detecting means. Accordingly, the affected part alone, for example, cancer cells can be effectively destroyed without adversely affecting the normal cells.

The value of the constant temperature, i.e., the predetermined temperature to be maintained constant by this automatic control operation, is determined by comparing the multiplying or reproducing speed of the malignant cells 38 of a cancer to the reproducing speed of the normal cells 48. At the thirty-first convention of the Japanese Society of Celular Biology as described earlier, the following experimental data was made public. According to this data, the cancer cells reproduced to fifty times their original number while the normal cells reproduced to 10 or more times at 37° C. However, at 39.5° C., the cancer cells stopped its reproduction after an interval of a week, but the normal cells still continued its reproduction. At 40° C., the cancer cells continued to reproduce up to the fourth day, and then abruptly started dying. Within three days thereafter, 80% had died, and the rest died by the eleventh day completely. In this period, it is reported that the normal cells continued to reproduce, and became 4 times their original number after an interval of a week. At 41° C., the cancer cells do not have the ability to reproduce at all, while the normal cells retain this ability. At 43° C., the normal cells continued to live for a week, and the cancer cells completely died within a day. According to this report, it is concluded that 39.5° C. is a critical temperature, and the temperature for destroying abnormal cells such as cancer cells must be above 39.5° C. It is to be noted, however, that this result is based on experiments in test tubes (*in vitro*). The predetermined temperature is thus determined based on various cases for practical use. In some cases, it is possible to destroy the cancer cells within a short period of time at a temperature above 43° C. However, in accordance with the present invention, the affected part 38 can be heated to a constant temperature regardless of the particular value selected as the predetermined temperature.

Although specific constructions have been illustrated and described herein, it is not intended that the invention be limited to the elements and constructions disclosed. One skilled in the art will recognize that other particular elements or subconstructions may be used without departing from the scope and spirit of the invention.

What is claimed is:

1. An endoscope for medical treatment of a body part, comprising:
   an endoscope having a distal end portion, said distal end portion including an observation optical system;
   a thermal energy generating means mounted on said distal end portion for providing thermal energy to the outside from said distal end portion for heating the body part to be treated;
   a temperature detecting means mounted on said distal end portion for detecting the temperature of the body part to be heated by said thermal energy and providing a detection signal which is a function of the detected temperature of said heated part, said temperature detecting means including:
      at least one heat-responsive element;
      at least one thermally conductive needle with said at least one heat-responsive element respectively built-in, said needle being normally totally within said distal end portion of said endoscope; and
      plunger means mounted at a predetermined position in said distal end portion of said endoscope for selectively displacing said at least one needle out of said distal end portion and toward the heated body part;
   said thermal energy generating means further including thermal insulating means for heat insulating said thermal energy generating means from said temperature detecting means for decreasing the amount of thermal energy leaked from said thermal energy generating means to said temperature detecting means; and
   control means coupled to said temperature detecting means for feedback controlling said thermal energy generating means in response to said detection signal for maintaining said heated body part at a predetermined temperature.

2. An endoscope of claim 1, wherein the thermal energy generating means provides thermal energy in the form of an electromagnetic wave of a frequency in a predetermined frequency range.

3. An endoscope of claim 2, wherein the electromagnetic wave is an infrared ray.

4. An endoscope according to any one of claims 1, 2, or 3 wherein said control means includes:
   (a) comparing means coupled to said temperature detecting means for comparing a signal corresponding to said detection signal with a reference signal corresponding to the predetermined temperature so as to provide a comparison result signal corresponding to the difference between the reference signal and said signal corresponding to said detection signal; and
   booster means coupled to said comparing means for boosting said comparison result signal so as to provide an output signal for driving said thermal energy generating means.

5. An endoscope according to any one of claims 2, or 3 wherein said endoscope includes an insertion section unitary with the distal end portion thereof; and said control means includes a control unit disposed inside said insertion section for feedback controlling said thermal energy generating means in response to the detection signal.

6. An endoscope of claim 5, further comprising an external power supply means coupled to the endoscope for supplying power to said control unit.

7. An endoscope of claim 1, wherein said adiabatic means comprises a heat insulating cylinder surrounding said thermal energy generating means at least at the distal end of said endoscope.

8. An endoscope for medical treatment of a body part, comprising:
   an endoscope having a distal end portion, said distal end portion including an observation optical system;
   a thermal energy generating means mounted on said distal end portion for providing thermal energy to the outside from said distal end portion for heating the body part to be treated;
   a temperature detecting means mounted on said distal end portion for detecting the temperature of the body part to be heated by said thermal energy and providing a detection signal which is a function of the detected temperature of said heated part;
   said temperature detecting means including at least one heat-responsive element; at least one thermally conductive needle with said at least one heat-responsive element respectively built-in, said needle being normally totally within said distal end portion of said endoscope; and plunger means mounted at a predetermined position in said distal end portion of said endoscope for selectively displacing said at least one needle out of said distal end portion and toward the heated body part; and
   control means coupled to said temperature detecting means for feedback controlling said thermal energy generating means in response to said detection signal for maintaining said heated body part at a predetermined temperature.

9. An endoscope of claim 8, wherein the thermal energy generating means provides thermal energy in the form of an electromagnetic wave of a frequency in a predetermined frequency range.

10. An endoscope of claim 9, wherein the electromagnetic wave is an infrared ray.

11. An endoscope according to any one of claims 8, 9, or 10, wherein said control means includes:
   comparing means coupled to said temperature detecting means for comparing a signal corresponding to said detection signal with a reference signal corresponding to the predetermined temperature so as to provide a comparison result signal corresponding to the difference between the reference signal and said signal corresponding to said detection signal; and
   booster means coupled to said comparing means for boosting said comparison result signal so as to provide an output signal for driving said thermal energy generating means.

12. An endoscope according to claim 8, wherein said control means includes:
   an insert part of the endoscope unitary with the distal end portion thereof; and
   a control unit disposed inside said insert part for feedback controlling the thermal energy generating means in response to the detected signal.

13. An endoscope of claim 12, further comprising power supply means coupled to the endoscope for supplying power to said control unit.

* * * * *

UNITED STATES PATENT AND TRADEMARK OFFICE
CERTIFICATE OF CORRECTION

PATENT NO. : 4,402,311
DATED : September 6, 1983
INVENTOR(S) : SHINICHIRO HATTORI It is certified that error appears in the above-identified patent and that said Letters Patent is hereby corrected as shown below:

COLUMN 9 (claim 5), lines 64-65, change "of claims 2, or 3" to

--of claims 1, 2, or 3,--;

COLUMN 10 (claim 7), line 6, change the word "adiabatic" to

--thermal insulating--.

Signed and Sealed this

Twenty-ninth Day of November 1983

[SEAL]

Attest:

GERALD J. MOSSINGHOFF

Attesting Officer    Commissioner of Patents and Trademarks